(12) United States Patent
Chakravarti et al.

(10) Patent No.: US 9,637,432 B2
(45) Date of Patent: May 2, 2017

(54) METHOD AND SYSTEM FOR PRODUCING METHANOL USING PARTIAL OXIDATION

(71) Applicants: Shrikar Chakravarti, East Amherst, NY (US); Minish Shah, East Amherst, NY (US); Raymond F. Drnevich, Clarence Center, NY (US)

(72) Inventors: Shrikar Chakravarti, East Amherst, NY (US); Minish Shah, East Amherst, NY (US); Raymond F. Drnevich, Clarence Center, NY (US)

(73) Assignee: PRAXAIR TECHNOLOGY, INC., Danbury, CT (US)

( * ) Notice: Subject to any disclaimer, the term of this patent is extended or adjusted under 35 U.S.C. 154(b) by 0 days.

(21) Appl. No.: 14/963,344

(22) Filed: Dec. 9, 2015

(65) Prior Publication Data

US 2016/0176793 A1    Jun. 23, 2016

Related U.S. Application Data

(60) Provisional application No. 62/093,048, filed on Dec. 17, 2014.

(51) Int. Cl.
*C07C 29/151* (2006.01)
*C07C 31/04* (2006.01)
*C01B 3/36* (2006.01)
*C01B 3/38* (2006.01)

(52) U.S. Cl.
CPC ............ *C07C 29/1518* (2013.01); *C01B 3/36* (2013.01); *C01B 3/382* (2013.01); *C01B 2203/025* (2013.01); *C01B 2203/0233* (2013.01); *C01B 2203/0244* (2013.01); *C01B 2203/061* (2013.01); *C01B 2203/0872* (2013.01); *C01B 2203/1258* (2013.01); *C01B 2203/141* (2013.01); *C01B 2203/142* (2013.01); *C01B 2203/148* (2013.01)

(58) Field of Classification Search
CPC ... C01B 3/382; C01B 3/36; C01B 2203/0872; C01B 2203/0244; C01B 2203/1258; C01B 2203/148; C01B 2203/025; C01B 2203/0233; C01B 2203/0141; C01B 2203/061; C01B 2203/142; C07C 29/158; C07C 31/04; C07C 29/1518
See application file for complete search history.

(56) References Cited

U.S. PATENT DOCUMENTS 6,495,609 B1 * 12/2002 Searle .................... C01B 31/20
                                                        518/700
2007/0004809 A1 * 1/2007 Lattner .................. C01B 3/382
                                                        518/700

* cited by examiner

*Primary Examiner* — Jafar Parsa
(74) *Attorney, Agent, or Firm* — Donald T. Black

(57) ABSTRACT

A method and system for producing methanol that employs steam methane reforming (SMR) and/or autothermal (ATR) synthesis gas production system, together with a partial oxidation system, is disclosed. The dual mode system and method for producing the synthesis gas in a methanol production process optimizes the efficiency and productivity of the methanol plant by using the partial oxidation based reforming system as an independent source of synthesis gas. The disclosed methods and systems are configurable either as a retrofit to existing methanol production facilities or as an integrated package into newly constructed methanol production facilities.

15 Claims, 3 Drawing Sheets

METHOD AND SYSTEM FOR PRODUCING METHANOL USING PARTIAL OXIDATION

CROSS REFERENCE RELATED APPLICATIONS

This application claims the benefit of priority to U.S. provisional application Ser. No. 62/093,048 filed on Dec. 17, 2014, the disclosure of which is incorporated by reference herein in its entirety.

FIELD OF THE INVENTION

The present invention relates to a method and system for producing methanol wherein partial oxidation or autothermal reforming of a hydrocarbon feed stream is incorporated into the method and system.

BACKGROUND

The methanol production process generally involves directing a compressed synthesis gas comprising hydrogen, carbon monoxide and carbon dioxide at an elevated temperature and pressure to a methanol converter reactor containing one or more beds of a methanol synthesis catalyst such as a copper and zinc oxide catalyst. The carbon monoxide and carbon dioxide in the synthesis gas react with the hydrogen to form methanol across the catalyst. The methanol synthesis process is usually operated in a loop where a portion of the compressed synthesis gas is converted to methanol each pass through the methanol converter reactor. Most of the unconverted gas is recycled to the methanol converter. A small portion is purged to prevent the buildup of inerts such as nitrogen, argon and methane. Methanol product is recovered by cooling the methanol product gas stream to a temperature below the dew point of the methanol such that a product composition comprising crude methanol and water condenses out, with the remaining gas being recycled through the methanol converter reactor. The crude methanol and water produced in the methanol converter reactor are typically reduced in pressure in a let-down or "flash" vessel. Since most crude methanol contains a range of impurities, including higher alcohols, the crude methanol must be purified so as to remove such impurities to produce methanol of chemical grade quality. The preferred technique used for methanol purification is a distillation process.

Synthesis gas used for methanol synthesis is typically characterized by the stoichiometric ratio $(H_2-CO_2)/(CO+CO_2)$, often referred to as the module or stoichiometric number, wherein $H_2$, $CO_2$ and CO denote the mole fractions of hydrogen, carbon dioxide and carbon monoxide, respectively, in the synthesis gas. A module of about 2.0 defines the desired stoichiometric ratio of synthesis gas for the production of methanol. Other important properties of the synthesis gas in methanol production include the carbon monoxide to carbon dioxide ratio and the concentration of inerts in the synthesis gas. A high carbon monoxide to carbon dioxide ratio typically increases the reaction rate of the formation of methanol and the achievable per pass conversion while it concurrently decreases the formation of water thereby reducing the catalyst deactivation rate. A high concentration of inerts in the synthesis gas, such as methane, argon, nitrogen, etc. typically lowers the partial pressure of the active reactants. Since the methanol conversion reaction is exothermic, lower temperatures favor conversion of the synthesis gas to methanol. Pressure will also affect the methanol conversion reaction, with increasing pressure also favoring methanol formation.

In many methanol production facilities, the incoming compressed synthesis gas is often mixed with recycled unreacted gas stream to form the synthesis gas stream that is supplied to the methanol converter reactor. A portion of the unreacted gas stream may be purged to prevent the buildup of inerts in the methanol converter reactor. The amount of purge flow typically varies anywhere from 1% to 10% of the total unreacted gas stream and often depends on the amount of inerts in the incoming synthesis gas, with higher level of inerts generally requiring higher purge flows and lower level of inerts generally requiring lower purge flows.

Some of the prior art uses of the purge stream include use of the hydrogen and/or methane slip in the purge stream as a feed or source of fuel to be used in the front-end steam methane reforming (SMR), partial oxidation (POx), autothermal reforming (ATR) processes. Other prior art has suggested the recovery of hydrogen from the purge stream and mixing the recovered hydrogen with the synthesis gas to improve the module of synthesis gas for methanol production.

As used herein, steam methane reforming (SMR) is a catalytic conversion of natural gas, including methane and light hydrocarbons, to synthesis gas containing hydrogen and carbon monoxide by reaction with steam. The reactions are endothermic, requiring significant amount of energy input. The steam methane reforming process is carried out at high temperatures within catalyst filled tubes inside a fired furnace. The amount of steam used is in excess of the reaction stoichiometry requirements, as required to prevent the catalyst from coking. No oxygen is used in steam methane reforming.

Partial oxidation, on the other hand, is a non-catalytic process where a sub-stoichiometric amount of oxygen is allowed to react with the natural gas creating steam and carbon dioxide at high temperatures. The residual methane is reformed through reactions with the high temperature steam and carbon dioxide to produce synthesis gas. In principle, the partial oxidation reaction can be carried out without any steam addition. Autothermal reforming is a variant of the partial oxidation process, but which uses a catalyst to permit reforming to occur at lower temperatures than the partial oxidation process. Moderate amounts of steam are typically required to prevent the catalyst from coking.

Many synthesis gas generation methods also employ pre-reforming and secondary reforming. When the feedstock contains significant amounts of heavy hydrocarbons, SMR and ATR processes are typically preceded by a pre-reforming step. As generally known in the art, pre-reforming is a catalyst based process for converting higher hydrocarbons to methane, hydrogen, carbon monoxide and carbon dioxide. The reactions involved in pre-reforming are typically endothermic. Most pre-reformers operate adiabatically, and thus the pre-reformed feedstock typically leaves at a lower temperature than the feedstock entering the pre-reformer. A secondary reforming process conventionally refers to an autothermal reforming process that is fed product from a SMR process. Thus, the feed to a secondary reforming process is primarily synthesis gas from the SMR. Depending on the end application, some natural gas may bypass the SMR process and be directly introduced into the secondary reforming process. Also, when a SMR process is followed by a secondary reforming process, the SMR may operate at a lower temperature, e.g. 650° C. to 800° C. versus 850° C. to 950° C.

SUMMARY OF THE INVENTION

The present invention may be characterized as a method for producing a product composition comprising methanol, comprising the steps of:

(i) producing a first stream of synthesis gas having a module greater than 2.0, in a steam methane reformer (SMR) or in a steam methane reformer followed by an autothermal reformer, by reforming a first hydrocarbon feed stream and steam in the presence of a catalyst;

(ii) producing a second stream of synthesis gas having a module less than that of the first stream of synthesis gas, by partial oxidation or autothermal reforming of a second hydrocarbon feed stream;

(iii) combining the first stream of synthesis gas and the second stream of synthesis gas to form a combined synthesis gas stream; and (iv) synthesizing the combined synthesis gas product stream in a methanol synthesis reactor into a product composition comprising methanol.

Preferably, the second stream of synthesis gas has a module of between about 1.4 and 2.0; a methane slip of less than about 4.5 percent by volume, and more preferably less than about 2.0 percent by volume; and a hydrogen to carbon monoxide ratio of between about 1.5 and 2.4.

The module of the combined synthesis gas stream that is directed to the methanol synthesis reactor is preferably between about 2.0 to 2.8. Also, all or a portion of the purge gas from the methanol synthesis section is preferably recycled to the SMR. In some embodiments, a portion of the purge gas may also be recycled to the partial oxidation based syngas generation system to be mixed with second hydrocarbon feed stream, or to be combusted as fuel to create a hot oxygen stream which is used in the partial oxidation or used as fuel for steam or power generation.

The source of oxygen used for generating the second stream of synthesis gas is preferably an air separation plant using cryogenic or VPSA technology and producing oxygen at a purity that ensures that the inert content of the second stream of synthesis gas is comparable to, i.e. up to 10 vol. % higher than, and preferably less than or equal to, the inert content of the first synthesis gas. This is typically achieved with oxygen purities in the range of 85-95%.

Another aspect of the present invention may be characterized as a method for enhancing the methanol output from an existing facility that produces a product composition comprising methanol, wherein the existing facility produces a first stream of synthesis gas from a pre-existing steam methane reformer (SMR) or a combined steam methane reformer followed by an autothermal reformer, by reforming a first hydrocarbon feed stream and steam in the presence of a catalyst, the method comprising the steps of:

(i) producing a second stream of synthesis gas, with a lower module than the first stream of synthesis gas, by partial oxidation or autothermal reforming of a second hydrocarbon feed stream;

(ii) combining the first stream of synthesis gas and the second stream of synthesis gas to form a combined synthesis gas stream with a module that is less than the module of the first synthesis gas stream; and (iv) synthesizing the combined synthesis gas product stream in a methanol synthesis reactor into a product composition comprising methanol.

The source of oxygen used for generating the second stream of synthesis gas is preferably an air separation plant using cryogenic or VPSA technology and producing oxygen at a purity that ensures that the inert content of the second synthesis gas is comparable to, i.e. up to 10 vol. % higher than, and preferably less than or equal to, the inert content of the first synthesis gas. This is typically achieved with oxygen purities in the range of 80-95%.

The purge rate in the methanol loop is adjusted so that the flowrate of the recycled unconverted gas stream to the methanol converter is comparable to the recycle rate in the pre-existing facility without the second synthesis gas stream.

BRIEF DESCRIPTION OF THE DRAWINGS

While the specification concludes with claims distinctly pointing out the subject matter that applicants regard as their invention, it is believed that the invention will be better understood when taken in connection with the accompanying drawings in which:

For the sake of avoiding repetition, some of the common elements in the various Figures utilize the same numbers where the explanation of such elements would not change from Figure to Figure.

DETAILED DESCRIPTION

Figure 1:
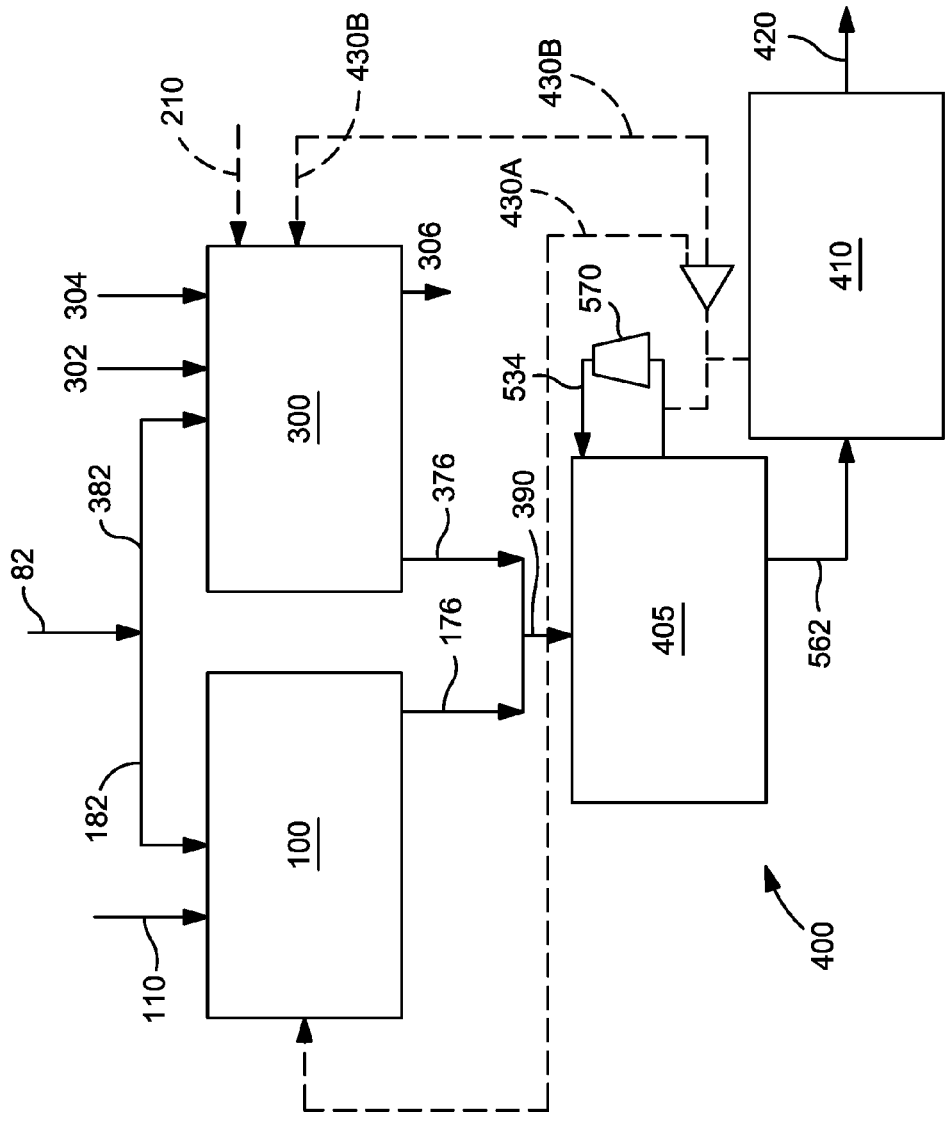
FIG. 1 is a schematic illustration of a methanol production process employing a partial oxidation or autothermal reforming based synthesis gas generation system and a conventional synthesis gas generation system, (e.g. SMR, combined reformer, i.e. SMR followed by ATR, etc.) in accordance with the present invention.

A preferred configuration or arrangement of coupling a partial oxidation based synthesis gas generation system to a methanol production process is shown in FIG. 1. As seen therein, the synthesis gas supplied to the methanol synthesis and purification system 400 is a combined synthesis gas stream 390 comprising the synthesis gas product stream 176 produced from a hydrocarbon containing feed stream 182 by the partial oxidation or autothermal reforming based synthesis gas generation system 100 and a synthesis gas stream 376 produced from a hydrocarbon containing feed stream 382 by a conventional synthesis gas generation system 300 such as a steam methane reformer (SMR); or combined reformer (SMR followed by an ATR). Oxidant stream 110 contains oxygen for the partial oxidation and/or autothermal reforming in system 100, and has an oxygen content of 20.9 vol. % (i.e. air) up to 80 vol. % or higher, even up to 99.5 to 100 vol. %. When an autothermal reformer is employed in system 300, oxidant stream 210 provides oxygen for the autothermal reformer. Oxidant stream 210 has an oxygen content of 20.9 vol. % (i.e. air) up to 100%.

In this arrangement, hydrocarbon containing feed stream 182 is received by the partial oxidation or autothermal reforming based synthesis gas generation system 100, as described herein. The two hydrocarbon containing feed streams 182 and 382 may be independent streams whose compositions are the same or different from each other or, as illustrated, may originate from a common hydrocarbon containing feed stream 82. A steam methane reformer employed as synthesis gas generation system 300 reacts hydrocarbons in feed stream 382 in conventional manner with steam 302 and with the input of heat (indicated as 304, which combines a fuel stream and oxygen containing stream such as air) as the steam methane reforming reaction is endothermic. This generates both a synthesis gas stream 376 and a flue gas 306.

The combined synthesis gas stream 390 is synthesized by known technology in a methanol converter reactor 405 into a crude methanol stream 562, which can be subsequently purified in a methanol purification system 410 into a higher purity methanol product 420. Preferably, the production of higher purity methanol is carried out in a manner that is integrated with the system that includes the methanol converter reactor 405 and the systems 100 and 300, as shown in FIG. 1. Alternatively, the crude methanol stream 562 can be conveyed to a facility not integrated with reactor 405, where it is then treated to recover higher purity methanol, which may be the final product or a precursor for production of other chemicals or liquid fuels. In another alternative, crude methanol stream 562 is fed to a reactor or other processing stage (such as another section of a petrochemical plant) such that recovery of a higher purity methanol product is not necessarily carried out.

To enhance the overall efficiency of the methanol plant, an unreacted portion 534 of stream 390 is usually recycled to the methanol converter reactor 405 via a circulator or compressor 570. In addition, purge streams 430A, 430B comprising unreacted hydrogen and methane slip are recycled from the methanol synthesis and purification system 400 to the conventional synthesis gas generation system 300 or partial oxidation or autothermal reforming based synthesis gas generation system 100 or both. This particular coupling arrangement, schematically shown in FIG. 1, is most suitable for the retrofit of existing natural gas based methanol production plants having a conventional synthesis gas production system, and where the partial oxidation or autothermal reforming based synthesis gas generation system is constructed as a retrofit to the existing methanol production plant and integrated therein.

System 100 converts most of the methane and higher hydrocarbons in feed stream 182 into a synthesis gas product stream 176 containing a number of components including hydrogen, carbon monoxide (CO), $CO_2$, $H_2O$ and unconverted $CH_4$.

Figure 2:
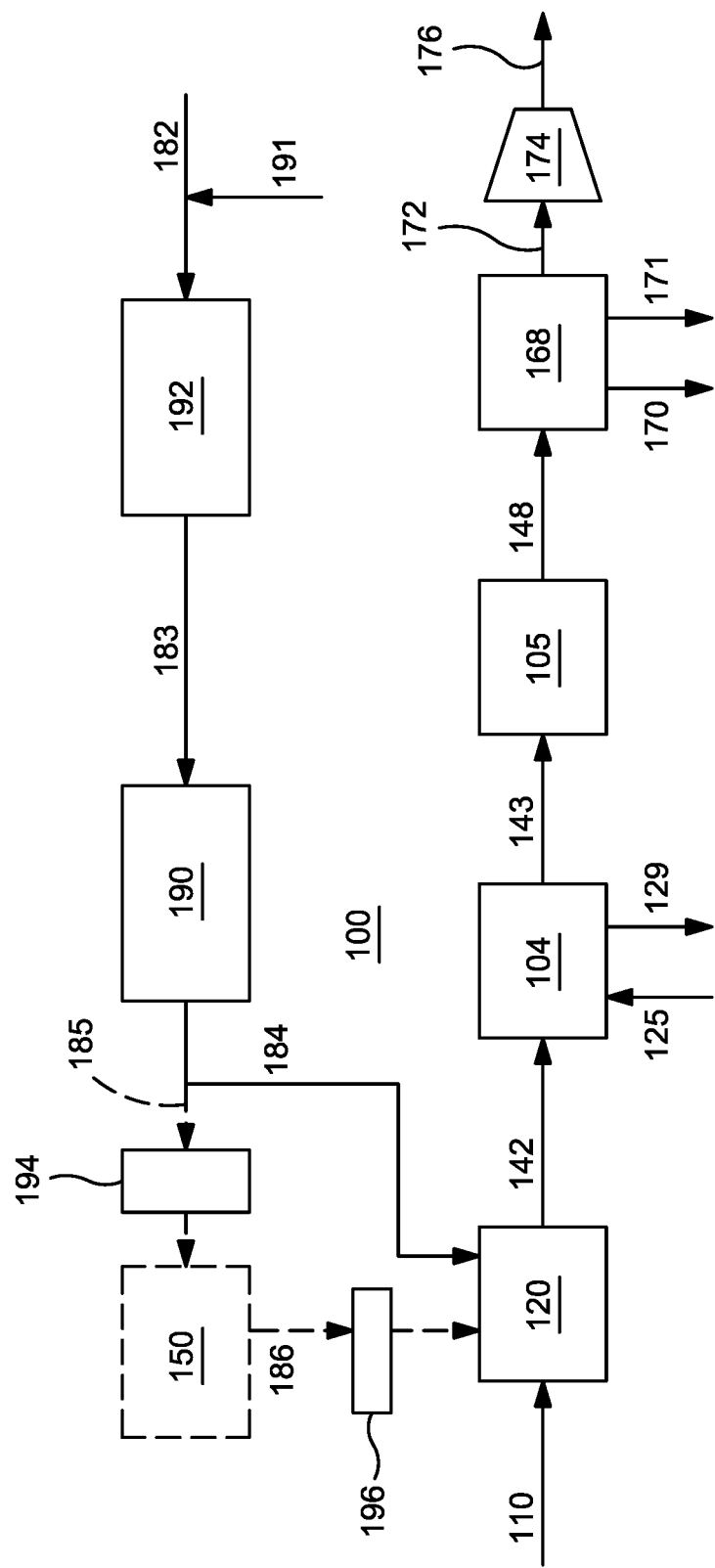
FIG. 2 is a schematic illustration of an embodiment of a partial oxidation or autothermal reforming based synthesis gas generation system in accordance with the present invention.

Turning now to FIG. 2, there is shown a schematic illustration of an embodiment of a partial oxidation or autothermal reforming based synthesis gas generation system 100 in accordance with the present invention.

Unit 120 denotes a reactor in which hydrocarbon feed stream 182 can be subjected to partial oxidation or to autothermal reforming. The details of the reactor and specific feed conditions can differ, depending on whether partial oxidation or autothermal reforming is being practiced, but are familiar to those skilled in this field.

The hydrocarbon containing feed stream 182 to be reformed is preferably natural gas but may be any suitable combustible fluid examples of which include methane, propane and coke oven gas, or a process stream containing reformable hydrocarbons. Depending on the supply pressure, the natural gas feed is compressed or let down to the desired pressure via a compressor or valve arrangement (not shown). Since natural gas typically contains unacceptably high levels of sulfur species, and where other feed material contains unacceptably high levels of sulfur species, desulfurization is required to prevent poisoning of catalyst used in an autothermal reforming step and/or in methanol synthesis.

To facilitate the desulfurization, a small amount of hydrogen or hydrogen-containing gas 191 is added to the feed stream 182. Stream 182 is then preheated in heat exchanger 192, that serves as a fuel preheater, to about 700° F. The resulting heated stream 183 undergoes sulfur removal in desulfurization unit 190, which typically includes a hydro-treating device to reduce the sulfur species to $H_2S$ and a guard bed using material like ZnO and/or CuO for removal of the $H_2S$. The hydro-treating step also saturates any alkenes present in the hydrocarbon containing feed stream. Since natural gas generally contains higher hydrocarbons that will break down at high temperatures to form unwanted carbon deposits that adversely impact catalyst-based reforming processes, the desulfurized natural gas feed stream 184 is mixed with superheated steam 185, heated to around 900° F. (e.g. heat exchanger 194) and pre-reformed in an adiabatic pre-reformer 150, which converts higher hydrocarbons to methane, hydrogen, carbon monoxide, and carbon dioxide. The pre-reformed gas 186, which is typically at a lower temperature than the feed to the prereformer, is preheated to about 1050° F. (e.g. in heat exchanger 196) and then sent to unit 120. When unit 120 is a partial oxidation unit, the addition of superheated steam, the pre-reforming, and the preheating are generally not required, and the desulfurized feed stream 184 could directly be fed to unit 120.

Though not explicitly shown in FIG. 1, the reforming system 300 used to generate the first synthesis gas stream 376, will typically include a fuel preheater and desulfurization unit. It may be possible to increase the size of these units, eliminate preheater heat exchanger 192 and desulfurization unit 190, and directly provide desulfurized natural gas 184 to unit 120 for generation of the second synthesis gas stream 176. For the case when the second stream 176 of synthesis gas is being generated to augment the methanol output of an existing facility, it is likely that a separate fuel preheater and desulfurizer may not be required since the design margin for these units may accommodate the additional flow associated with hydrocarbon containing feed stream 182.

Partial oxidation involves reaction between hydrocarbon (such as natural gas or methane) and oxidant (e.g. air, oxygen-enriched air having an oxygen content from above that of air to 80 vol. % or higher, or oxygen recovered from air and having an oxygen content of 80 vol. % or higher). In partial oxidation, the hydrocarbon containing stream 182 and the oxygen in the oxidant stream 110 are introduced into a partial oxidation reactor, and they react with each other. The amount of oxygen fed is less than the stoichiometric amount that would be required for complete conversion of the hydrocarbon feed to carbon dioxide and water. The residence time in the reactor is typically less than about 4 seconds. The reaction is exothermic and produces heat. Temperatures in the reaction zone typically increase to above 2370° F. The high temperatures allow the following reforming reactions to occur without a catalyst in the reactor:

$$CH_4 + H_2O \Rightarrow CO + 3H_2$$

$$2CH_4 + O_2 \Rightarrow 2CO + 4H_2$$

$$CO_2 + H_2 \Rightarrow CO + H_2O$$

In autothermal reforming, oxygen reacts with hydrocarbons in a natural gas and steam containing feed in a first reaction zone formed by a burner. The exothermic oxidation reaction releases heat to support the endothermic steam methane reforming reactions in a catalyst filled zone. Use of catalysts facilitate reforming reactions to occur at lower temperatures relative to the partial oxidation case. Exit temperature of the syngas from an autothermal reformer is typically in the range of 1700° F.-1900° F. versus 2300° F.-2700° F. for a partial oxidation unit.

The synthesis gas 142 produced by partial oxidation or autothermal reforming in unit 120 generally contains hydrogen, carbon monoxide, carbon dioxide, water and other constituents such as unconverted methane. The hot synthesis gas is cooled in heat exchange sections 104 and 105 and treated to remove substances that should not be present when the stream is fed to reactor 405 in the methanol synthesis section. Section 104 typically includes a quench and/or process gas boiler that cools the synthesis gas 142 to less than about 760° F. Streams 125 and 129 represent the cooling water input and water/steam output from section 104, respectively. This initially cooled synthesis gas 143 is successively further cooled in heat exchange section 105, which removes heat from the gas by indirect heat exchange such as via the hydrocarbon feed heater 192, an economizer, feedwater heater, or air and/or water based synthesis gas coolers.

The resultant cooled synthesis gas 148 is fed to unit 168 which represents a conditioning stage to remove water 170 and/or impurities 171 that may be present such as particulates (e.g. soot), acid gases including $CO_2$, ammonia, sulfur species, HCN and other inorganic substances such as alkali compounds. Impurities may be removed in one stage or in a series of stages each intended to remove different ones of these impurities that are present or to reduce specific contaminants to the desired low levels. The fully cooled synthesis gas stream 172 is compressed in compressor unit 174 to produce synthesis gas product stream 176. Depending on the operating pressure of the methanol converter, typically in the range of 1000-1500 psia, multiple stages of compression may be required in unit 174. Any inter-stage cooling and condensate knock-out stages in unit 174 are not shown in FIG. 2.

The resulting cooled, conditioned gaseous stream 176 contains at least hydrogen, carbon monoxide and carbon dioxide. The exact composition of syngas stream 176 depends on a number of factors including:

Type of syngas generation unit 120 (partial oxidation or autothermal reforming),
Operating conditions of unit 120 (pressure, temperature),
Composition of feed stream 182 and amount of added steam 185, and
Amount and oxygen content of oxidant stream 110.

In particular, the content of inert components (such as $N_2$, Ar and $CH_4$) of stream 176 is significantly impacted by the oxygen content of the oxidant stream 110. A key feature of this invention is to ensure that the inert content of the synthesis gas stream 176 is comparable to, preferably equal to or less than, the inert content of first synthesis gas stream 376. While these criteria can easily be met by using a high purity (>95%) oxygen stream, this invention is especially useful when implemented using a low purity (<95%) oxygen stream. Streams of the desired suitable oxygen content can be provided either by a VPSA plant or a cryogenic plant appropriately set up to provide an oxidant stream having the desired oxygen content. A low purity plant generally provides a significant reduction in capital and operating costs versus a high purity plant. Furthermore, use of a VPSA plant providing about 90% $O_2$, may allow for a further reduction in capital cost due to its modularity and ease of installation.

Figure 3:
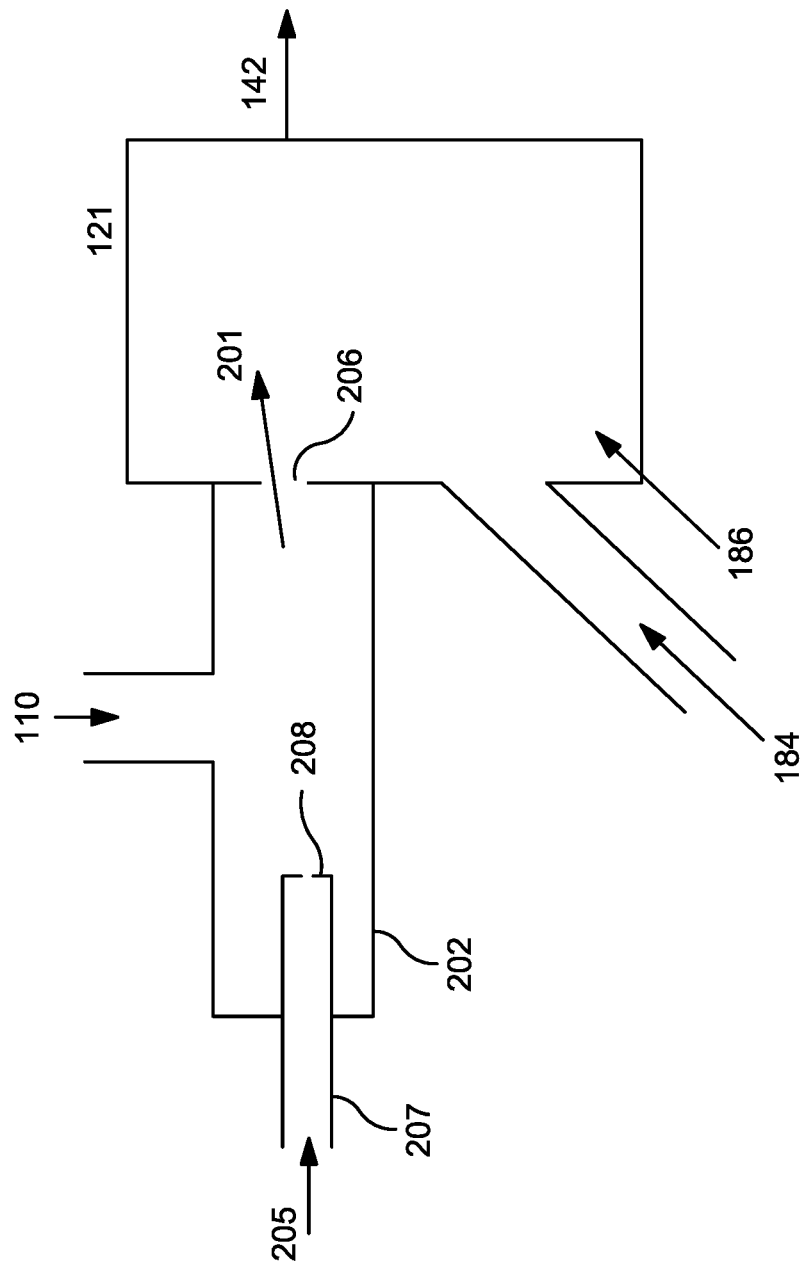
FIG. 3 is a schematic illustration of a hot oxygen generator useful in the practice of the present invention.

FIG. 3 illustrates a preferred embodiment of partial oxidation unit 120 (FIG. 2) that uses a hot oxygen generator 202 to generate a high velocity, hot oxygen stream 201 to reform the desulfurized feed stream 184 (and/or desulfurized and prereformed stream 186, if present) in a reaction chamber 121. The hot oxygen burner enhances mixing, accelerates oxidation kinetics, and accelerates the kinetics of the reforming of methane in the feed stream 184 (and/or stream 186 if present). Stream 110 of oxidant preferably having an oxygen concentration of at least 30 volume percent and more preferably at least 80 volume percent is provided into a hot oxygen generator 202, which is preferably a chamber or duct having an inlet 204 for the oxidant 110 and having an outlet nozzle 206 for the stream 201 of hot oxygen. The oxidant 110 fed to the hot oxygen generator 202 has an initial velocity which is generally within the range of from 50 to 300 feet per second (fps) and typically will be less than 200 fps.

Stream 205 of fuel is provided into the hot oxygen generator 202 through a suitable fuel conduit 207 ending with nozzle 208 which may be any suitable nozzle generally used for fuel injection. The fuel may be any suitable combustible fluid examples of which include natural gas, methane, propane, hydrogen and coke oven gas, or may be a portion of feed stream 182 or 184, or a portion of a process stream such as synthesis gas streams 176 or 376, or a portion or all of purge stream 430A (seen in FIG. 1). Preferably the fuel is a gaseous fuel. Liquid fuels such as number 2 fuel oil or a liquid byproduct stream (e.g. higher alcohols, ethers and/or ketones) from the methanol synthesis and purification sections may also be used, although it would be harder to maintain good mixing and reliable and safe combustion with a liquid fuel rather than with a gaseous fuel.

The amount of oxygen fed in stream 110 must be in stoichiometric excess relative to the total amount of combustible matter ("fuel") fed in stream 205. The fuel fed in stream 205 provided into the hot oxygen generator 202 combusts therein with oxidant 110 to produce heat and combustion reaction products such as carbon dioxide and water vapor.

The heat of combustion generated upon combustion of the fuel in the hot oxygen generator 202 heats the uncombusted oxygen therein and raises its temperature. The combustion reaction products generated in the hot oxygen generator 202 mix with the unreacted oxygen of the oxidant 110, thus also providing heat to the remaining oxygen and raising its temperature. Preferably, the fuel 205 is provided into the hot oxygen generator 202 at a velocity that is suitable to sustain a stable flame for the particular arrangement of nozzle 208 within generator 202. The velocity of the fuel at nozzle 208 serves to entrain oxidant into the combustion reaction thus establishing a stable flame. The fuel velocity enables further entraining of combustion reaction products and oxidant into the combustion reaction, this improving the mixing of the hot combustion reaction products with the remaining oxygen within the hot oxygen generator 202 and thus more efficiently heating the remaining oxygen. Information about the formation of a high velocity hot oxygen stream 201 can also be found in U.S. Pat. No. 5,266,024.

Generally the temperature of remaining oxidant within the hot oxygen generator 202 is raised by at least about 500° F., and preferably by at least about 1000° F. The hot oxygen stream 201 obtained in this way is passed from the hot oxygen generator 202 into reaction chamber 121 through a suitable opening or nozzle 206 as a high velocity hot oxygen stream having a temperature of at least 2000° F. Generally the velocity of the hot oxygen stream will be within the range of from 500 to 4500 feet per second (fps), and will typically exceed the velocity of stream 203 by at least 300 fps.

The composition of the hot oxygen stream 201 depends on the conditions under which the stream is generated, but preferably it contains at least 50 vol. % $O_2$. This hot oxygen stream 201 facilitates the effective reforming/partial oxidation of feed stream 184. On a dry basis, the unconverted methane content of the generated synthesis gas is less than 1 vol. % and typically less than 0.5 vol. %. Thus, even with use of low purity oxygen, e.g. composition of stream 110 is 90% O2, 5% Ar, 5% N2, it is possible to generate the second synthesis gas stream 176 with an inert level of less than 4 vol. %, typically comparable to that of the first synthesis gas stream 376. The module of synthesis gas stream 176 is typically between about 1.4 and 2.0.

The following example is used to highlight key aspects of the invention.

EXAMPLE

This example illustrates the implementation of the present invention in a natural gas ("NG") to methanol conversion facility which originally has an SMR system for syngas generation. With reference to FIG. 1, this SMR system is unit 300, and there is no unit 100.

61.1 MMSCFD of NG is fed to the SMR system 300. 218.3 MMSCFD of syngas (corresponding to stream 376) is generated and fed to the methanol conversion reactor (corresponding to 405). Composition of stream 376 is provided in the table below. This syngas has a module of 2.9, $H_2$/CO ratio of 5 and contains 3.6 mol % of inerts. Methanol output from the facility is 2000 short tons/day. About 1087 MMSCFD of the unreacted gas stream from the methanol synthesis converter is compressed and recycled as stream 534. The remaining 58 MMSCFD is used as fuel stream 430B for the SMR system 300.

The existing SMR-based methanol facility is subsequently retrofitted with a partial oxidation system 100 in parallel with the SMR system 300. An additional 11.2 MMSCFD of NG is fed to the partial oxidation system. About 280 tons/day of oxygen at 90% purity (5% Ar, 5% N2) is fed to system 100. This oxygen could be supplied by either a cryogenic or VPSA system. The partial oxidation system 100 generates 28.4 MMSCFD of a second or supplemental synthesis gas stream 176. Composition of stream 176 is provided in the table below. This second synthesis gas stream has a module of 1.6, $H_2$/CO ratio of 1.8 and an inert content of 3 mol. %.

The two synthesis gas streams 176 and 376 are combined to form synthesis gas stream 390, that is fed to the methanol synthesis unit. The module of the combined synthesis gas stream 390 is 2.7. Total methanol output from this facility is increased by 20% to 2400 tons/day. Specific NG consumption decreases by 1.4% implying an improvement in overall process efficiency as well. However, the unreacted gas flow for this case is comparable to that for the base case without the partial oxidation syngas generation system. This is due to the improved quality, i.e. reduced module, of the synthesis gas, which increases per pass conversion. The methanol loop recycle flow is similar to that for the base SMR case implying that existing compressor 570 can continue to be used as is. Additional compression is not required. The purge is again used as fuel stream 430B for the SMR system 300. No purge is sent to the partial oxidation system 100.

| | Stream # in FIG. 1 | Base – SMR | Bolt-on POx Unit | SMR + POx |
|---|---|---|---|---|
| Key inputs: | | | | |
| NG, MMSCFD | 382/182/82 | 61.1 | 11.2 | 72.3 |
| O2, tons/day | | 110 | 280 | 280 |
| Key outputs: | | | | |
| MeOH, tons/day | | 420 | 2000 | — | 2400 |
| Syngas to MeOH synthesis, MMSCFD | 376/176/390 | 218.3 | 28.4 | 246.7 |
| Syngas Compostion (mol. %) | | | | |
| H2 | | 73.4% | 60.4% | 71.9% |
| CO | | 14.7% | 34.6% | 17.0% |
| CO2 | | 7.9% | 1.8% | 7.2% |
| N2 | | 0.2% | 1.6% | 0.4% |
| H2O | | 0.4% | 0.2% | 0.3% |
| Ar | | 0.0% | 1.3% | 0.2% |
| CH4 | | 3.4% | 0.1% | 3.0% |
| Module of syngas | | 2.9 | 1.6 | 2.7 |
| H2/CO ratio of syngas | | 5.0 | 1.8 | 4.2 |
| Inert content of syngas, mol % | | 3.6% | 3.0% | 3.5% |
| MeOH Loop Recycle Flow, MMSCFD | 534 | 1087 | — | 1089 |
| MeOH Loop Purge Flow, MMSCFD | 430B | 58 | — | 58 |
| NG consumption, scf/ton MeOH | | 30,530 | — | 30,106 |

What is claimed is:

1. A method for producing a product composition comprising methanol, comprising the steps of
   (i) producing a first stream of synthesis gas having a module greater than 2.0, in a steam methane reformer (SMR) or in a steam methane reformer followed by an autothermal reformer, by reforming a first hydrocarbon feed stream and steam in the presence of a catalyst;
   (ii) producing a second stream of synthesis gas having a module less than that of the first stream of synthesis gas, by partial oxidation or autothermal reforming of a second hydrocarbon feed stream;
   (iii) combining the first stream of synthesis gas and the second stream of synthesis gas to form a combined synthesis gas stream; and
   (iv) synthesizing the combined synthesis gas product stream in a methanol synthesis reactor into a product composition comprising methanol;
   and further comprising the step of recycling a portion of the excess hydrogen and methane slip formed during synthesis of the product composition comprising methanol to the steam methane reformer.

2. The method of claim 1 wherein the second stream of synthesis gas is produced by autothermal reforming of the second hydrocarbon feed stream.

3. The method of claim 1 wherein the second stream of synthesis gas is produced by partial oxidation of the second hydrocarbon feed stream.

4. The method of claim 3 wherein the second stream of synthesis gas is produced by partial oxidation of the second hydrocarbon feed stream with a high velocity stream of hot oxygen.

5. The method of claim 1 wherein the second stream of synthesis gas has a module of between about 1.4 and 2.0.

6. The method of claim 1 wherein the second stream of synthesis gas has a methane slip of less than about 4.5 percent by volume.

7. The method of claim 1 wherein the module of the combined synthesis gas stream is between about 2.0 to 2.8.

8. The method of claim 1 wherein said second stream of synthesis gas is produced by reaction of said second hydrocarbon feed stream with oxygen that is comprised in an oxidant having an oxygen content of at least 80 vol. %.

9. The method of claim 1 further comprising the step of cooling one or both of the first stream of synthesis gas or the second stream of synthesis gas to a temperature of about 400° C. or less.

10. The method of claim 1 wherein a combined hydrocarbon feed stream is treated to lower the content therein of sulfur compounds, and a portion of the resulting treated hydrocarbon feed stream comprises said first hydrocarbon feed stream and another portion of the resulting treated hydrocarbon feed stream comprises said second hydrocarbon feed stream.

11. A method for enhancing the methanol output from an existing facility that produces a product composition comprising methanol, wherein the existing facility produces a first stream of synthesis gas from a pre-existing steam methane reformer (SMR) or a combined steam methane reformer followed by an autothermal reformer, by reforming a first hydrocarbon feed stream and steam in the presence of a catalyst, the method comprising the steps of:

(i) producing a second stream of synthesis gas, with a lower module than the first stream of synthesis gas, by partial oxidation or autothermal reforming of a second hydrocarbon feed stream;

(ii) combining the first stream of synthesis gas and the second stream of synthesis gas to form a combined synthesis gas stream with a module that is less than the module of the first synthesis gas stream; and (iv) synthesizing the combined synthesis gas product stream in a methanol synthesis reactor into a product composition comprising methanol;

and further comprising the step of recycling a portion of the excess hydrogen and methane slip formed during synthesis of the product composition comprising methanol to the steam methane reformer.

12. The method of claim 11 wherein the second stream of synthesis gas has a module of between about 1.4 and 2.0.

13. The method of claim 11 wherein the second stream of synthesis gas has a methane slip of less than about 4.5 percent by volume.

14. The method of claim 11 wherein the module of the combined synthesis gas stream is between about 2.0 to 2.8.

15. The method of claim 11 wherein said second stream of synthesis gas is produced by reaction of said second hydrocarbon feed stream with oxygen that is comprised in an oxidant having an oxygen content of at least 80 vol. %.

* * * * *